(12) United States Patent
Louwagie et al.

(10) Patent No.: US 12,311,187 B2
(45) Date of Patent: May 27, 2025

(54) BATTERY ASSEMBLY FOR MEDICAL DEVICE

(71) Applicant: Medtronic, Inc., Minneapolis, MN (US)

(72) Inventors: Jeffrey J. Louwagie, Minnetonka, MN (US); Paul B. Aamodt, Prior Lake, MN (US); Vincent Brama, Minnetonka, MN (US); Nicholas H. Finstrom, Elk River, MN (US); Michael B. Hintz, Mahtomedi, MN (US); Vadim A. Yakovlev, Brooklyn Park, MN (US); Kevin D. O'Connell, Lino Lakes, MN (US); Richard W. Swenson, Edina, MN (US); Brian P. Schmidt, Andover, MN (US); Joseph J. Viavattine, Vadnais Heights, MN (US); Puqiang Zhang, Plymouth, MN (US); Hailiang Zhao, Plymouth, MN (US); Chao Hu, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 319 days.

(21) Appl. No.: 17/812,506

(22) Filed: Jul. 14, 2022

(65) Prior Publication Data
US 2022/0347485 A1 Nov. 3, 2022

Related U.S. Application Data

(62) Division of application No. 16/841,157, filed on Apr. 6, 2020, now Pat. No. 11,413,466.
(Continued)

(51) Int. Cl.
*A61N 1/375* (2006.01)
*A61N 1/378* (2006.01)
(Continued)

(52) U.S. Cl.
CPC .......... *A61N 1/3758* (2013.01); *A61N 1/378* (2013.01); *H01M 10/0436* (2013.01);
(Continued)

(58) Field of Classification Search
CPC ..... A61N 1/3758; A61N 1/378; A61N 1/3975
See application file for complete search history.

(56) References Cited

U.S. PATENT DOCUMENTS 4,294,891 A * 10/1981 Yao .................... H01M 8/08
429/523
5,419,982 A 5/1995 Tura et al.
(Continued)

FOREIGN PATENT DOCUMENTS

EP 1798787 A2 6/2007
EP 3405257 A1 11/2018
(Continued)

OTHER PUBLICATIONS

Advisory Action from U.S. Appl. No. 16/530,470 dated Sep. 14, 2022, 3 pp.
(Continued)

*Primary Examiner* — Eugene T Wu
(74) *Attorney, Agent, or Firm* — Shumaker & Sieffert, P.A.

(57) ABSTRACT

In some examples, a battery assembly for an implantable medical device. The battery assembly may include an electrode stack comprising a plurality of electrode plates, wherein the plurality of electrode plates comprises a first electrode plate including a first tab extending from the first electrode plate and a second electrode plate including a second tab extending from the second electrode plate; a spacer between the first tab and the second tab; and a rivet extending through the first tab, second tab, and spacer,
(Continued)

wherein the rivet is configured to mechanically attach the first tab, second tab, and spacer to each other.

20 Claims, 11 Drawing Sheets

Related U.S. Application Data

(60) Provisional application No. 62/835,738, filed on Apr. 18, 2019.

(51) Int. Cl.
| | | |
|---|---|---|
| *H01M 10/04* | (2006.01) | |
| *H01M 50/474* | (2021.01) | |
| *H01M 50/54* | (2021.01) | |
| *H01M 50/477* | (2021.01) | |

(52) U.S. Cl.
CPC ......... *H01M 50/474* (2021.01); *H01M 50/54* (2021.01); *H01M 50/477* (2021.01)

(56) References Cited

U.S. PATENT DOCUMENTS

| | | | |
|---|---|---|---|
| 6,032,075 | A | 2/2000 | Pignato et al. |
| 7,035,078 | B1 | 4/2006 | Viavattine |
| 7,111,882 | B2 | 9/2006 | Corscadden et al. |
| 7,179,562 | B2 | 2/2007 | Zolotnik et al. |
| 7,479,349 | B2 | 1/2009 | O'phelan et al. |
| 7,564,677 | B2 | 7/2009 | Poplett |
| 8,133,604 | B1 | 3/2012 | Nakahara et al. |
| 8,236,411 | B2 | 8/2012 | Waki et al. |
| 8,236,441 | B2 | 8/2012 | Gardner et al. |
| 8,614,017 | B2 | 12/2013 | Viavattine |
| 8,841,020 | B2 | 9/2014 | Viavattine |
| 10,693,119 | B2 | 6/2020 | Wyser et al. |
| 11,065,460 | B2 | 7/2021 | Zhao et al. |
| 11,413,466 | B2 | 8/2022 | Louwagie et al. |
| 2003/0171784 | A1 | 9/2003 | Dodd et al. |
| 2003/0199942 | A1 | 10/2003 | Nielsen et al. |
| 2006/0096082 | A1* | 5/2006 | Aamodt ............ H01G 9/08 |
| | | | 429/246 |
| 2006/0096958 | A1 | 5/2006 | Zhao et al. |
| 2006/0166088 | A1 | 7/2006 | Hokanson et al. |
| 2006/0222942 | A1 | 10/2006 | Zhao et al. |
| 2006/0238960 | A1 | 10/2006 | Poplett |
| 2009/0197160 | A1 | 8/2009 | Fujiwara et al. |
| 2009/0197180 | A1 | 8/2009 | Viavattine et al. |
| 2009/0208816 | A1 | 8/2009 | Viavattine et al. |
| 2011/0152959 | A1 | 6/2011 | Sherwood et al. |
| 2012/0107670 | A1 | 5/2012 | Viavattine |
| 2013/0131744 | A1 | 5/2013 | Viavattine |
| 2013/0131745 | A1 | 5/2013 | Viavattine |
| 2015/0136840 | A1 | 5/2015 | Zhao et al. |
| 2019/0081313 | A1 | 3/2019 | Wyser et al. |
| 2020/0330774 | A1 | 1/2020 | Louwage et al. |
| 2021/0031046 | A1 | 2/2021 | Zhao |

FOREIGN PATENT DOCUMENTS

| | | |
|---|---|---|
| EP | 3457453 A1 | 3/2019 |
| WO | 2017127149 A1 | 7/2017 |

OTHER PUBLICATIONS

International Search Report and Written Opinion of International Application No. PCT/US2020/027573, mailed Jul. 13, 2020, 11 pp.
Ayosa, "Swaging: A Deformation," MISUMI Blog—Mechanical Design, Mar. 7, 2018, accessed from https://us.misumi-ec.com/blog/swaging-a-deformation/, accessed on Dec. 7, 2021, 10 pp.
Prosecution History from U.S. Appl. No. 16/426,849, now issued U.S. Pat. No. 11,065,460, dated Oct. 5, 2020 through Mar. 26, 2021, 40 pp.
Prosecution History from U.S. Appl. No. 16/530,470, dated Aug. 20, 2021 through Aug. 3, 2022, 70 pp.
Prosecution History from U.S. Appl. No. 16/841,157, now issued U.S. Pat. No. 11,413,466, dated Nov. 12, 2021 through Jul. 22, 2022, 20 pp.
U.S. Appl. No. 62/835,738, by Jeffrey J. Louwagie et al., filed Apr. 18, 2019.
Communication pursuant to Article 94(3) EPC from counterpart European Application No. 20722916.2 dated Aug. 13, 2024, 5 pp.
Observation of a third party pursuant to Art. 115 EPC, counterpart European Application No. 20722916.2, dated May 1, 2024, 6 pp.

\* cited by examiner

BATTERY ASSEMBLY FOR MEDICAL DEVICE

This application is a divisional of U.S. patent application Ser. No. 16/841,157, filed Apr. 6, 2020, which claims the benefit of U.S. Provisional Patent Application No. 62/835,738, filed Apr. 18, 2019. The entire content of each of these applications is incorporated herein by reference.

TECHNICAL FIELD

The disclosure relates to batteries and, more particularly, to batteries of medical devices.

BACKGROUND

Medical devices such as implantable medical devices (IMDs) include a variety of devices that deliver therapy (such as electrical simulation or drugs) to a patient, monitor a physiological parameter of a patient, or both. IMDs typically include a number of functional components encased in a housing. The housing is implanted in a body of the patient. For example, the housing may be implanted in a pocket created in a torso of a patient. The housing may include various internal components such as batteries and capacitors to deliver energy for therapy delivered to a patient and/or to power circuitry for monitoring a physiological parameter of a patient and controlling the functionality of the medical device.

SUMMARY

In some aspects, the disclosure is directed to battery assemblies for use, e.g., in a medical device, and techniques for manufacturing the battery assemblies.

In one example, the disclosure is directed to a battery assembly for an implantable medical device. The assembly may comprise an electrode stack comprising a plurality of electrode plates, wherein the plurality of electrode plates comprises a first electrode plate including a first tab extending from the first electrode plate and a second electrode plate including a second tab extending from the second electrode plate; a spacer between the first tab and the second tab; and a rivet extending through the first tab, second tab, and spacer, wherein the rivet is configured to mechanically attach the first tab, second tab, and spacer to each other. In another example, the disclosure is directed to an implantable medical device comprising such a battery assembly within an outer housing of the implantable medical device, and processing circuitry, wherein the processing circuitry is configured to control delivery electrical therapy from the implantable medical device to a patient using power supplied by the battery assembly.

In another example, the disclosure is directed to a battery assembly for an implantable medical device. The assembly may comprise a battery housing; an electrode stack comprising a plurality of electrode plates, wherein the plurality of electrode plates including a first tab stack of anode tabs extending from anode plates of the electrode stack and a second tab stack of cathode tabs extending from cathodes plates of the electrode stack, wherein the first tab stack is adjacent to the second tab stack and a gap separates the first tab stack from the second tab stack; and a shim located on a top tab of at least one of the first tab stack or the second tab stack, wherein the shim is located between the at least one of the first tab stack or the first tab of the second tab stack and the battery housing. In another example, the disclosure is directed to an implantable medical device comprising such a battery assembly within an outer housing of the implantable medical device, and processing circuitry, wherein the processing circuitry is configured to control delivery electrical therapy from the implantable medical device to a patient using power supplied by the battery assembly.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
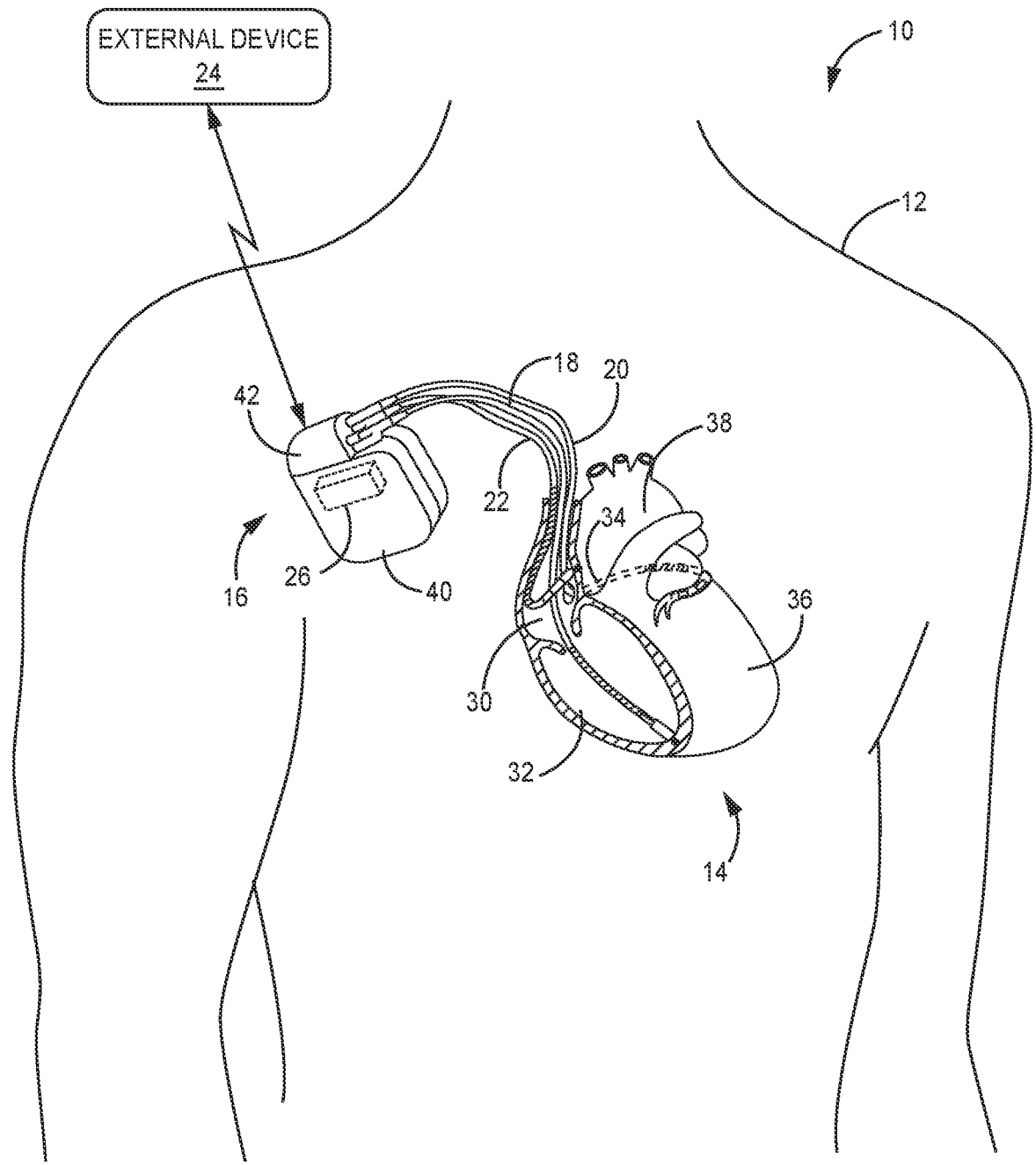
FIG. 1 is a conceptual diagram that illustrates an example medical device system that may be used to deliver therapy to a patient.

A variety of medical devices may utilize one or more batteries as a power source for operational power. For example, an implantable medical device (IMD) that provides cardiac rhythm management therapy to a patient may include a battery to supply power for the generation of electrical therapy or other functions of the IMD. For ease of illustration, examples of the present disclosure will be described primarily with regard to batteries employed in IMDs that provide cardiac rhythm management therapy. However, as will be apparent from the description herein, examples of the disclosure are not limited to IMDs that provide such therapy. For example, in some instances, one or more of the example batteries describe herein may be used by a medical device configured to deliver electrical stimulation to a patient in the form of neurostimulation therapy (e.g., spinal cord stimulation therapy, deep brain stimulation therapy, peripheral nerve stimulation therapy, peripheral nerve field stimulation therapy, pelvic floor stimulation therapy, and the like). In some examples, example batteries of this disclosure may be employed in medical device configured to monitor one or more patient physiological parameters, e.g., by monitoring electrical signals of the patient, alone or in conjunction with the delivery of therapy to the patient.

In some examples, a battery of an IMD may include a plurality of electrode plates (e.g., including both anode and cathode plates) stacked on each other in which each of the plates includes a tab extending therefrom. The tabs of the anode plates may be aligned with each other in a stack and electrically connected to each other to form an anode of the battery. In this sense, the tab stack may function as an electrical interconnect between the plates of the anode. Similarly, the tabs of the cathode plates may be aligned with each other in a stack and electrically connected to each other to form a cathode of the battery. In some examples, such a battery may be referred to as a flat plate battery.

In some examples, in each the anode tab stack and cathode tab stack, a spacer may be located between adjacent individual tabs in the stack of tabs, e.g., such that each individual tab is separated from an adjacent tab by a spacer. The spacers may be electrically conductive to electrically couple the respective tabs in the stack to each other and define an electrical interconnect, at least in part, between respective plates of the electrode. For each electrode, the tabs in the stack of tabs and spacers may be attached to each other by one or more side laser welds that span the height of the tab stack.

In some examples, the tabs of an electrode stack may be flexed or bent due to the nature of the spacer and tab interconnect design. This results in stressed materials that can lead to failures of the side weld(s) and/or insulation failures.

In some examples, a stacked plate battery interconnect spacer stack may be subject to "fanning" (e.g., opening like the pages of a bound book) as a result of the mechanical force applied by the expansion of the electrode stack, e.g., during discharge of the battery. The applied force may displace the spacer stack causing electrical shorting to the surrounding battery enclosure, and/or leading to failure of the laser welds on the interconnect spacer stack.

In some examples, the laser welds on the side of an interconnect spacer stack are subject to mechanical loading, e.g., when the electrode stack expands during battery life. The electrode stack expansion may be due to plate warp or cathode expansion during battery discharge. As described above, the mechanical loading on the interconnect spacer stack may result in the interconnect spacer stack "fanning" open much like when a book and its many pages are opened.

In accordance with at least some examples of the disclosure, a battery assembly that includes an electrode tab stack may include spacers of varying thicknesses and/or may include multiple spacers between individual tabs. The spacer and tab stacking sequence may be tailored to provide for desired flexing/bending that reduces material stresses in the interconnect and nearby electrode materials. In some examples, a predictive model may be employed to predict a desirable stacking sequence, e.g., using spacers of desired thicknesses. In some examples, the model may consider sources of variation in the components used to create the battery assembly. For example, the modeling may be used to assess the variation in thickness of the spacers and the associated tabs. The model may be used to strategically place the spacers based on inferred variation or measured variation in each component of the stacked assembly.

Additionally, or alternatively, a battery assembly in accordance with some examples of the disclosure may include a rivet through an aperture in the tab/spacer stack, (e.g., through a hole in or near the center of the stack of tabs). The rivet may prevent the mechanical "fanning" of the spacers. The rivet can be a piece of wire that is mechanically fastened and/or laser welded to the outer most plate tabs (e.g., the top and bottom tabs of the tab stack) of the stack assembly. The rivet may be configured to counter-act the forces applied by the electrode stack expansion.

Additionally, or alternatively, a battery assembly in accordance with some examples of the disclosure may include one or more spacers (also referred to as a shim) between the interconnect spacer tab stack and the surrounding battery housing (e.g., between the top of the spacer tab stack and the surrounding battery housing). In some examples, the shim may be formed of a polymer material that acts as an electrical insulator to prevent electrical shorting. The shim consumes space between the interconnect spacer stack and the enclosure wall, thus limiting the "fanning" that imparts stress on the laser welds. The shim may transfer the forces of electrode expansion away from the interconnect laser weld joint and impart those forces to the more robust battery housing walls.

In some examples, the shim may be a relatively simple molded polymer component that is added during assembly, or it can be designed as an integral feature of another insulator (e.g. headspace insulator, stack insulator, and/or feedthrough insulator). In some examples, the "shim" may be attached as a foldable feature that allows assembly ease, while also preventing occurrences of the shim inadvertently not being installed during battery assembly.

FIG. 1 is a conceptual diagram that illustrates an example medical device system 10 that may be used to provide electrical therapy to a patient 12. Patient 12 ordinarily, but not necessarily, will be a human. System 10 may include an IMD 16, and an external device 24. In the example illustrated in FIG. 1, IMD 16 has battery 26 positioned within an outer housing 40 of the IMD 16. Battery 26 may be a primary or secondary battery.

While the examples in the disclosure are primarily described with regard to battery 26 positioned within housing 40 of IMD 16 for delivery of electrical therapy to heart of patient 12, in other examples, battery 26 may be utilized with other implantable medical devices. For example, battery 26 may be utilized with an implantable drug delivery device, an implantable monitoring device that monitors one or more physiological parameter of patient 12, an implantable neurostimulator (e.g., a spinal cord stimulator, a deep brain stimulator, a pelvic floor stimulator, a peripheral nerve stimulator, or the like), or the like. Moreover, while examples of the disclosure are primarily described with regard to implantable medical devices, examples are not limited as such. Rather, some examples of the batteries described herein may be employed in any medical device including non-implantable medical devices. For example, an example battery may be employed to supply power to a medical device configured delivery therapy to a patient externally or via a transcutaneously implanted lead or drug delivery catheter.

In the example depicted in FIG. 1, IMD 16 is connected (or "coupled") to leads 18, 20, and 22. IMD 16 may be, for example, a device that provides cardiac rhythm management therapy to heart 14, and may include, for example, an implantable pacemaker, cardioverter, and/or defibrillator that provides therapy to heart 14 of patient 12 via electrodes coupled to one or more of leads 18, 20, and 22. In some examples, IMD 16 may deliver pacing pulses, but not cardioversion or defibrillation shocks, while in other examples, IMD 16 may deliver cardioversion or defibrillation shocks, but not pacing pulses. In addition, in further examples, IMD 16 may deliver pacing pulses, cardioversion shocks, and defibrillation shocks. IMD 16 may include electronics and other internal components necessary or desirable for executing the functions associated with the device. In one example, IMD 16 includes one or more of processing circuitry, memory, a signal generation circuitry, sensing circuitry, telemetry circuitry, and a power source. In general, memory of IMD 16 may include computer-readable instructions that, when executed by a processor of the IMD, cause it to perform various functions attributed to the device herein. For example, processing circuitry of IMD 16 may control the signal generator and sensing circuitry according to instructions and/or data stored on memory to deliver therapy to patient 12 and perform other functions related to treating condition(s) of the patient with IMD 16.

IMD 16 may include or may be one or more processors or processing circuitry, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" and "processing circuitry" as used herein may refer to any of the foregoing structure or any other structure suitable for implementation of the techniques described herein.

Memory may include any volatile or non-volatile media, such as a random-access memory (RAM), read only memory (ROM), non-volatile RAM (NVRAM), electrically erasable programmable ROM (EEPROM), flash memory, and the like. Memory may be a storage device or other non-transitory medium.

The signal generation circuitry of IMD 16 may generate electrical therapy signals that are delivered to patient 12 via electrode(s) on one or more of leads 18, 20, and 22, in order to provide pacing signals or cardioversion/defibrillation shocks, as examples. The sensing circuitry of IMD 16 may monitor electrical signals from electrode(s) on leads 18, 20, and 22 of IMD 16 in order to monitor electrical activity of heart 14. In one example, the sensing circuitry may include switching circuitry to select which of the available electrodes on leads 18, 20, and 22 of IMD 16 are used to sense the heart activity. Additionally, the sensing circuitry of IMD 16 may include multiple detection channels, each of which includes an amplifier, as well as an analog-to-digital converter for digitizing the signal received from a sensing channel (e.g., electrogram signal processing by processing circuitry of the IMD).

Telemetry circuitry of IMD 16 may be used to communicate with another device, such as external device 24. Under the control of the processing circuitry of IMD 16, the telemetry circuitry may receive downlink telemetry from and send uplink telemetry to external device 24 with the aid of an antenna, which may be internal and/or external.

The various components of IMD 16 may be coupled to a power source such as battery 26. Battery 26 may be a lithium primary battery or lithium secondary (rechargeable) battery although other types of battery chemistries are contemplated. Battery 26 may be capable of holding a charge for several years. In general, battery 26 may supply power to one or more electrical components of IMD 16, such as, e.g., the signal generation circuitry, to allow IMD 16 to deliver therapy to patient 12, e.g., in the form of monitoring one or more patient parameters, delivery of electrical stimulation, or delivery on a therapeutic drug fluid. Battery 26 may include a lithium-containing anode and cathode including an active material that electrochemically reacts with the lithium within an electrolyte to generate power. A wide variety of battery types and Leads 18, 20, 22 that are coupled to IMD 16 may extend into the heart 14 of patient 12 to sense electrical activity of heart 14 and/or deliver electrical therapy to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. In other examples, IMD 16 may deliver therapy to heart 14 from an extravascular tissue site in addition to or instead of delivering therapy via electrodes of intravascular leads 18, 20, 22. In the illustrated example, there are no electrodes located in left atrium 36. However, other examples may include electrodes in left atrium 36.

IMD 16 may sense electrical signals attendant to the depolarization and repolarization of heart 14 (e.g., cardiac signals) via electrodes (not shown in FIG. 1) coupled to at least one of the leads 18, 20, and 22. In some examples, IMD 16 provides pacing pulses to heart 14 based on the cardiac signals sensed within heart 14. The configurations of electrodes used by IMD 16 for sensing and pacing may be unipolar or bipolar. IMD 16 may also deliver defibrillation therapy and/or cardioversion therapy via electrodes located on at least one of the leads 18, 20, and 22. IMD 16 may detect arrhythmia of heart 14, such as fibrillation of ventricles 32 and 36, and deliver defibrillation therapy to heart 14 in the form of electrical shocks. In some examples, IMD 16 may be programmed to deliver a progression of therapies (e.g., shocks with increasing energy levels), until a fibrillation of heart 14 is stopped. IMD 16 may detect fibrillation by employing one or more fibrillation detection techniques known in the art. For example, IMD 16 may identify cardiac parameters of the cardiac signal (e.g., R-waves, and detect fibrillation based on the identified cardiac parameters).

In some examples, external device 24 may be a handheld computing device or a computer workstation. External device 24 may include a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. External 24 can additionally or alternatively include a peripheral pointing device, such as a mouse, via which a user may interact with the user interface. In some embodiments, a display of external 24 may include a touch screen display, and a user may interact with programmer 24 via the display.

A user, such as a physician, technician, other clinician or caregiver, or the patient, may interact with external device 24 to communicate with IMD 16. For example, the user may interact with external device 24 to retrieve physiological or diagnostic information from IMD 16. A user may also interact with external device 24 to program IMD 16 (e.g., select values for operational parameters of IMD 16).

External device 24 may communicate with IMD 16 via wireless communication using any techniques known in the art. Examples of communication techniques may include, for example, low frequency or radiofrequency (RF) telemetry, but other techniques are also contemplated. In some examples, external device 24 may include a communication head that may be placed proximate to the patient's body near the IMD 16 implant site in order to improve the quality or security of communication between IMD 16 and external device 24.

In the example depicted in FIG. 1, IMD 16 is connected (or "coupled") to leads 18, 20, and 22. In the example, leads 18, 20, and 22 are connected to IMD 16 using the connector block 42. For example, leads 18, 20, and 22 are connected to IMD 16 using the lead connector ports in connector block 42. Once connected, leads 18, 20, and 22 are in electrical contact with the internal circuitry of IMD 16. Battery 26 may be positioned within the housing 40 of IMD 16. Housing 40 may be hermetically sealed and biologically inert. In some examples, housing 40 may be formed from a conductive material. For example, housing 40 may be formed from a material including, but not limited to, titanium, stainless steel, among others.

Figure 2:
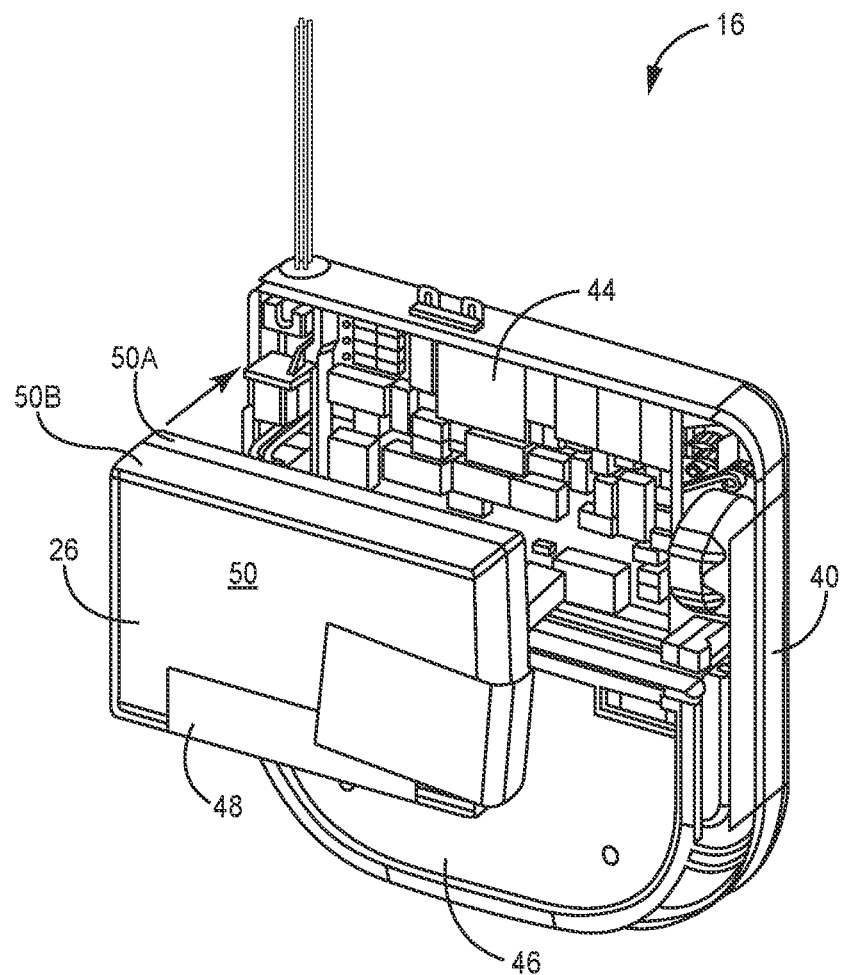
FIG. 2 is a conceptual diagram illustrating a partial exploded view of the IMD of FIG. 1.

FIG. 2 is a conceptual diagram of IMD 16 of FIG. 1 with connector block 42 not shown and a portion of housing 40 removed to illustrate some of the internal components within housing 40. IMD 10 includes housing 40, a control circuitry 44 (which may include processing circuitry), battery 26 (e.g., an organic electrolyte battery) and capacitor(s) 46. Control circuitry 44 may be configured to control one or more sensing and/or therapy delivery processes from IMD 16 via leads 18, 20, and 22 (not shown in FIG. 2). Battery 26 includes battery assembly housing 50 and insulator 48 (or liner) disposed therearound. Battery 26 charges capacitor(s) 46 and powers control circuitry 44.

Figure 3:
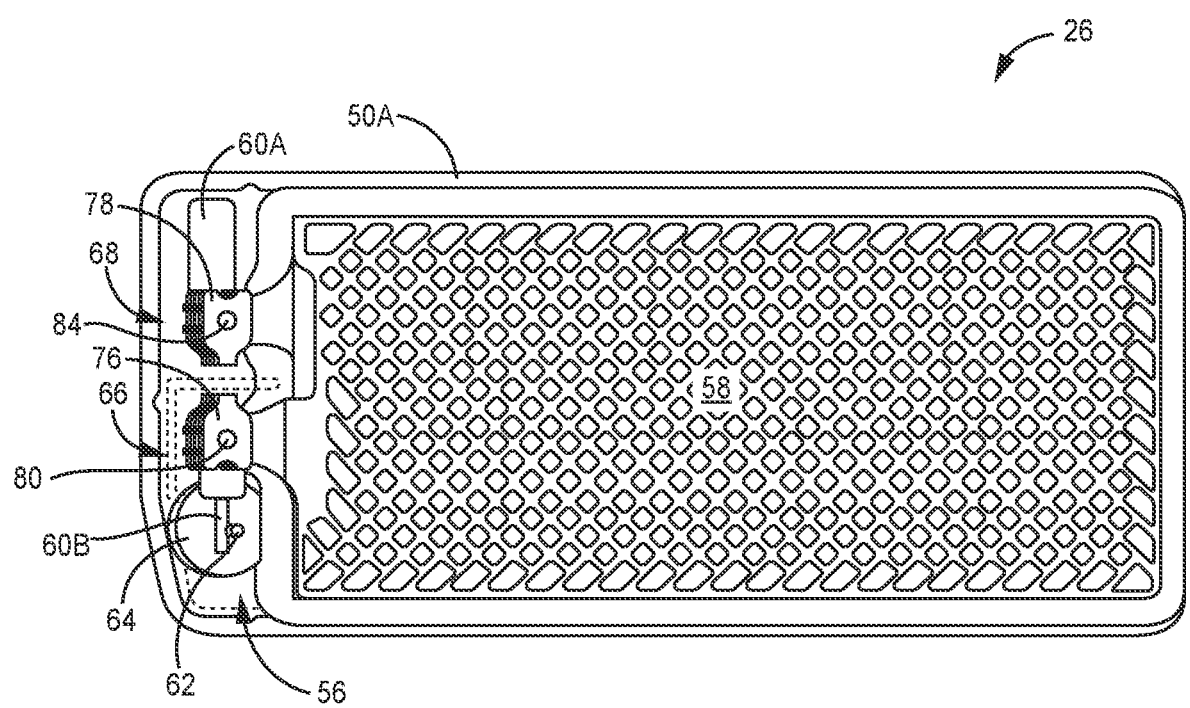
FIGS. 3 and 4 are conceptual diagrams illustrating portions of an example battery assembly in accordance with examples of the disclosure.
Figure 4:
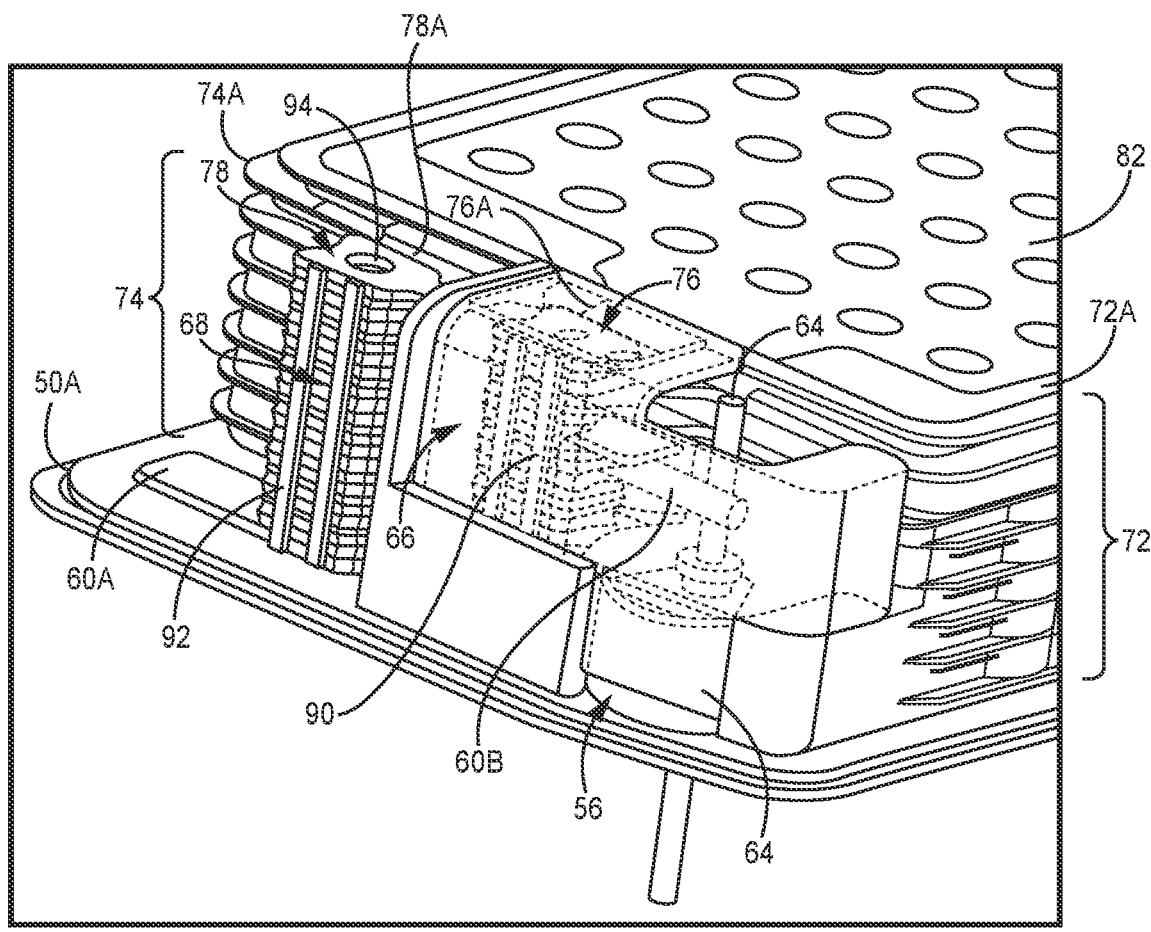

FIGS. 3 and 4 are conceptual diagrams illustrating aspect of example battery 26. Battery 26 includes assembly housing 50 having a bottom housing portion 50A and top housing portion 50B (shown in FIG. 2), a feed-through terminal 56, and an electrode assembly 58. An electrolyte may be filled into via a fill port (not shown) in housing 50. Housing 50 houses electrode assembly 58 with the electrolyte. Top portion 50B and bottom portion 50A of housing may be welded or otherwise attached to seal the enclosed components of battery 26 within housing 50. Feed-through assembly 56, formed by pin 62 and insulator member/ferrule 64, is electrically connected to jumper pin 60B. The connection between pin 62 and jumper pin 60B allows delivery of positive charge from electrode assembly 58 to electronic components outside of battery 26.

As noted above, a fill port (not shown) allows for the introduction of liquid electrolyte to electrode assembly 58. The electrolyte creates an ionic path between the anode(s) and the cathode(s) of electrode assembly 58. The electrolyte serves as a medium for migration of ions between the anode(s) and the cathode(s) during an electrochemical reaction with these electrodes.

Electrode assembly 58 is depicted as a stacked assembly. The anode(s) comprise a set of electrode plates 72 (including individual anode electrode plate 76A) with a set of tabs 76 (including individual tab 76A) extending therefrom that are conductively coupled via a conductive coupler 80 (also referred to as an anode collector). Although not labeled, the one or more spacers (e.g., conductive spacers) may be located between respective tabs in the set of tabs 76. The conductive coupler 80 may be a pin that extends vertically through the set of tabs 76 and spacers located between respective tabs. Additionally, or alternatively, one or more welds 90 may also conductively couple the set of tabs 76 and spacers. In accordance with at least some of examples of the disclosure, as described below, conductive coupler 80 may be a rivet that extends vertically through set of tabs 76 and spacers that also mechanically attaches the individual tabs 76 and spacers to each other.

Each anode electrode plate 72A includes a current collector or grid 82, a tab 76A extending therefrom, and an electrode material. The electrode material (or anode material) may include elements from Group IA, IIA or IIIB of the periodic table of elements (e.g. lithium, sodium, potassium, etc.), alloys thereof, intermetallic compounds (e.g. Li—Si, Li—B, Li—Si—B etc.), or an alkali metal (e.g. lithium, etc.) in metallic form.

Cathode tabs 68 may be constructed in a similar manner as anode tabs 66. The cathodes include a set of electrode plates 74 (including individual cathode electrode plates 74A) with a set of tabs 78 (including individual tab 78A) extending therefrom. As labelled in FIG. 5, e.g., one or more spacers (e.g., conductive spacers 86A-86C) may be located between respective tabs in the set of tabs 78. The conductive coupler 84 connects the set of tabs 78 and spacers 86. Conductive coupler 84 or other cathode collector may be connected to conductive member 60A. Conductive member 60A, shaped as a spacer plate, may comprise titanium, aluminum/titanium clad metal or other suitable materials. Conductive member 60A allows cathode tabs 68 to be electrically coupled to electronic components outside of battery 26. Each tab of the set of tabs 78 (including, e.g., individual tab 78A) may be additionally, or alternatively, attached to each other via laser weld(s) 92.

In accordance with at least some of examples of the disclosure, as described below, conductive coupler 84 may be a rivet that extends vertically through set of tabs 78 and spacers 86 that also mechanically attaches the individual tabs 76 and spacers 86 to each other.

Each cathode electrode plate 74A includes a current collector (not shown) or grid, an electrode material and a tab 78A extending therefrom. Tab 78A comprises conductive material (e.g., aluminum, etc.). Tab 78A comprises conductive material (e.g., copper, titanium, aluminum, etc.). Electrode material (or cathode material) may include metal oxides (e.g., vanadium oxide, silver vanadium oxide (SVO), manganese dioxide, etc.), carbon monofluoride and hybrids thereof (e.g., CFx+MnO2), combination silver vanadium oxide (CSVO), lithium ion, other rechargeable chemistries, or other suitable compounds.

Figure 5:
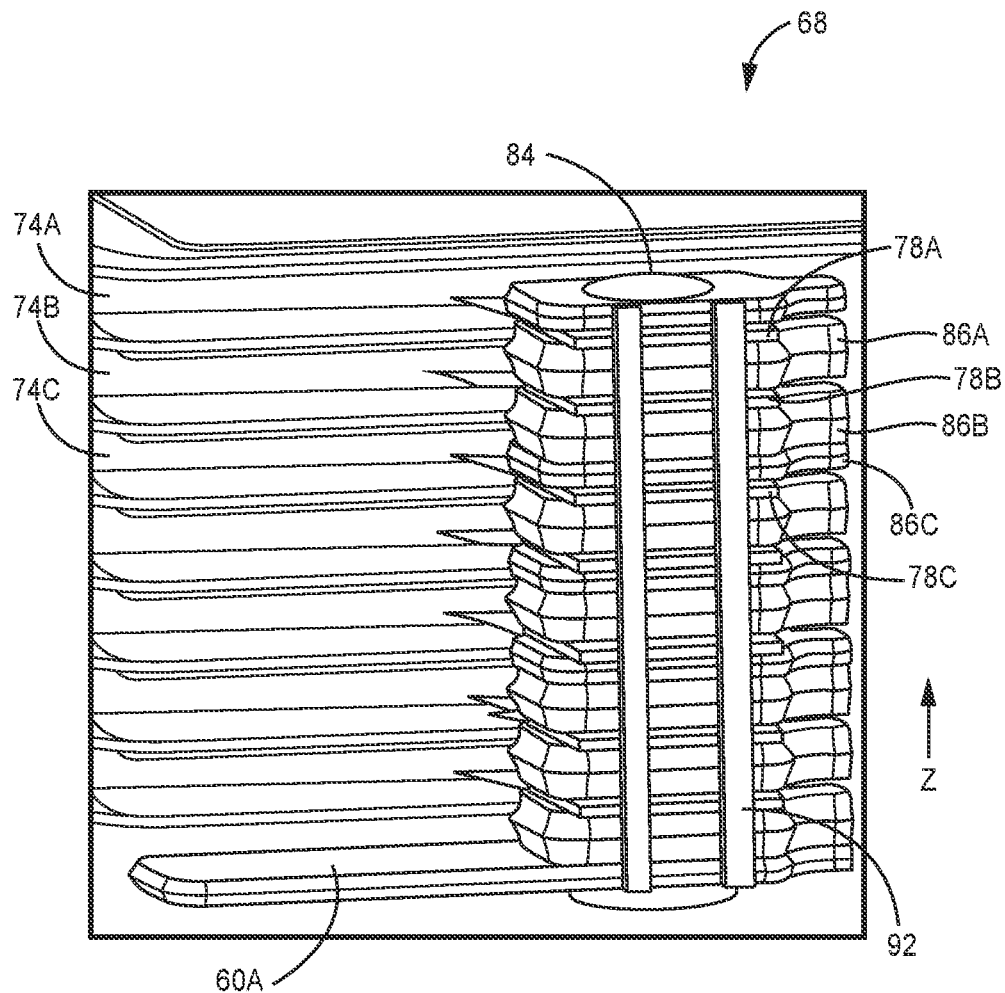
FIG. 5 is a conceptual diagram illustrating a portion of an example battery assembly including a stack of tabs and spacers of an electrode.
Figure 6:
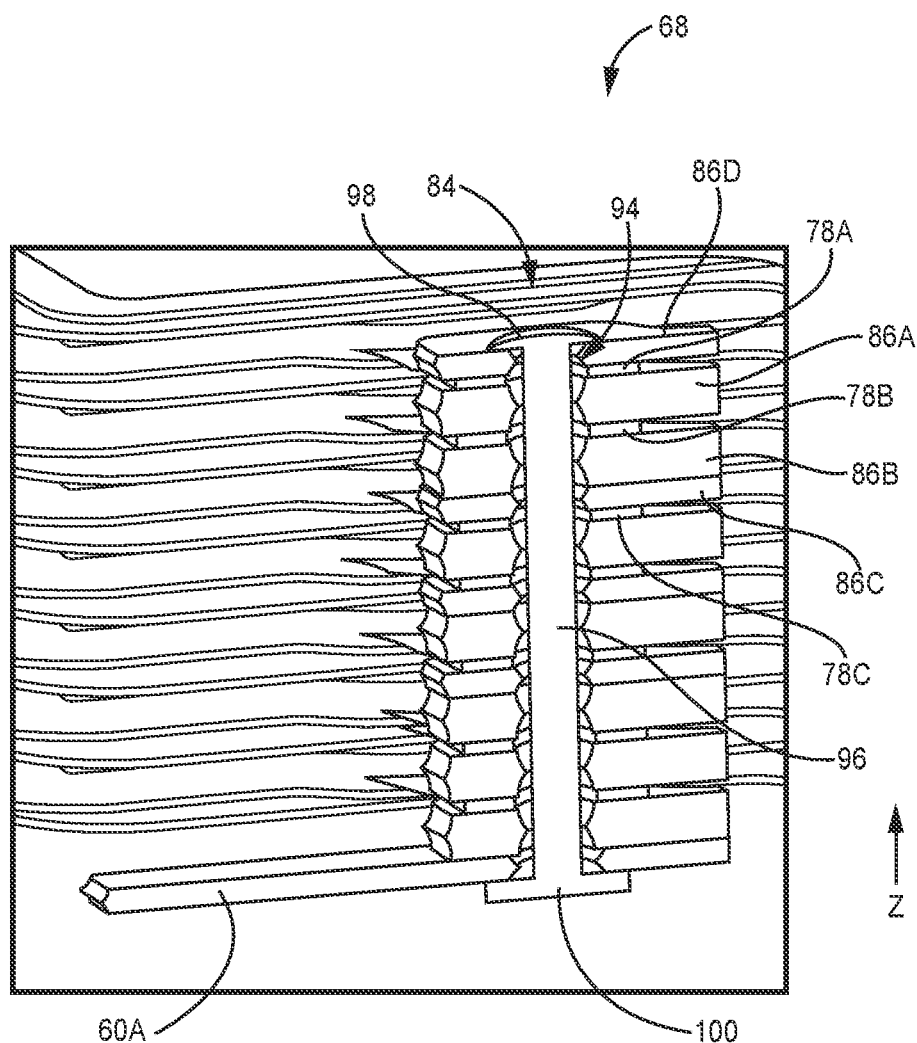
FIG. 6 is a conceptual diagram illustrating a cross-sectional view of the stack of tabs and spacers of FIG. 5.

FIG. 5 is a conceptual schematic diagram illustrating a magnified view of a portion of cathode tabs 68 of battery 26. FIG. 6 is a cross-section view of the stack of cathode tabs 78 shown in FIG. 5. As shown, electrodes plates 74 of cathode 66 includes cathode electrode plates 74A, 74B, 74C (among others) in a stacked configuration. Cathode tabs 78A, 78B, 78C extend from cathode electrodes plates 74A, 74B, 74C, respectively, and exhibit the same stacked configuration as electrode plate 74. At least one spacer is located between each respective tab. For example, spacer 86A is located between tabs 78A and tab 78B, and two spacers 86B and 86C are located between tab 78B and tab 78C.

For ease of description and illustration, not all the tabs and spacers of cathode stack 68 are labelled in FIGS. 5 and 6. However, it is understood that the description of tabs 78A-78C and spacers 86A-86C also may apply to any of the tabs and spacers shown in FIGS. 5 and 6. Additionally, while FIG. 5 is described with regard to cathode stack 68 it is contemplated that the same configuration is applicable to anode stack 66 of battery 26 shown in FIG. 3.

In some examples, spacer 86A ensures tabs 78A and 78B are substantially straight extending from plates 74A and 74B, respectively, and are not bent during a subassembly process to connect the set of tabs 78 (including, e.g., individual tab 78A) for cathode stack 68. While a single spacer 86A is depicted as being placed between two tabs, more than one spacer may be placed between two tabs, such as, e.g., spacers 86B and 86C between tabs 78B and 78C.

Spacers 86A-86C may comprise a conductive material, e.g., such that the each of the tabs are electrically interconnected. For electrode plates related to anode stack 66, titanium and alloys thereof or other suitable materials are used. For electrode plates related to cathode stack 68, titanium, nickel, aluminum, alloys thereof or other suitable materials are used.

Spacers 86A-86C may include a variety of shapes. Exemplary spacers include a substantially H-shaped spacer, substantially rectangular, circular, or include at least one triangular shape (e.g. a single triangle, a hexagon etc.). Spacers 86A-86C may have different or substantially the same individual thicknesses in the z-direction labeled in FIG. 5, e.g., to achieve different design criteria. For example, a thicker electrode plate may requires a thicker spacer. In the example in of FIG. 5, spacer 86A may have substantially the same thickness of spacer 86B but spacer 86C may be thinner than spacers 86A and 86B. In some examples, the thickness of a spacer may range from about 0.005 inches to about 0.030 inches although other values are contemplated. Examples of spacers 86A-86C may include one or more of the example spacers described in U.S. Published Patent Application 2009/0197180.

In some examples, the number of spacers and thicknesses of the individual spacer(s) between the tabs of cathode stack 68 and anode stack 66 may be selected such that tab bending is minimized yet still fits in the battery housing 50.

Figure 8:
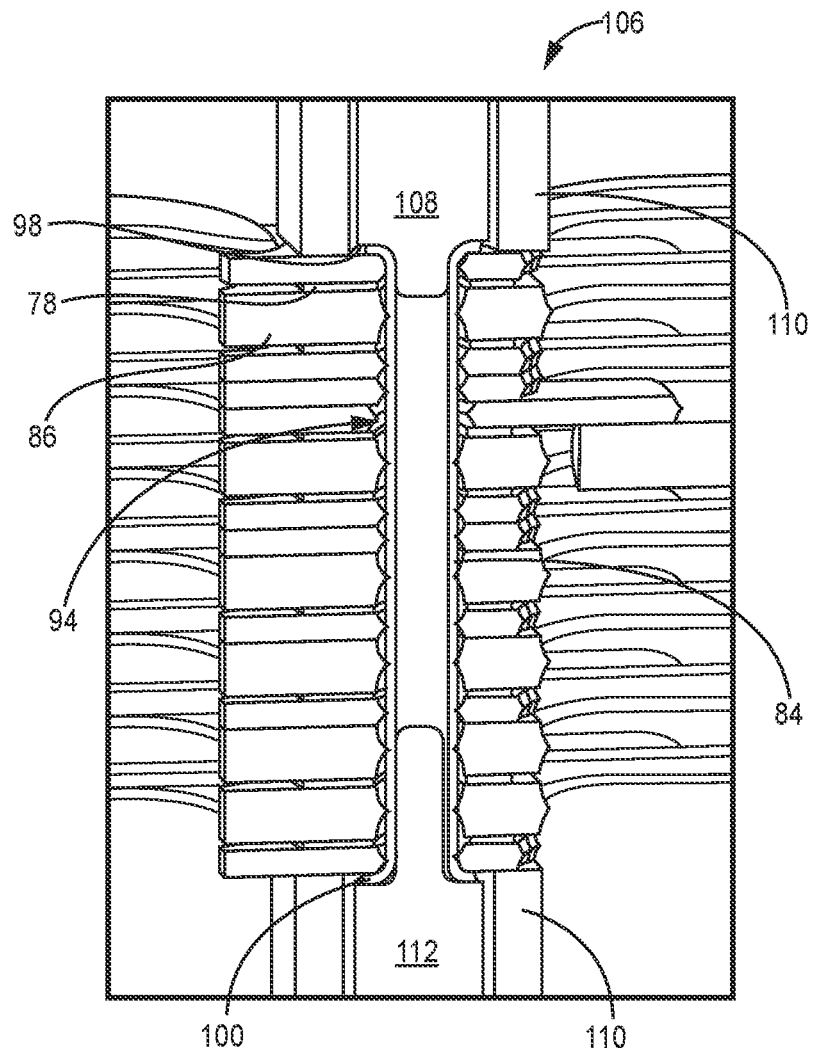
FIG. 8 is a conceptual diagram illustrating an example assembly for forming a battery assembly including a rivet.

As shown in FIGS. 5 and 6, cathode stack 68 may include rivet 84 extending through aperture 94 (shown in FIG. 4) that runs through the set of cathode tabs 78 (including, e.g., individual tab 78A), spacers 86, and conductive plate 60A in the z-direction. Rivet 84 includes body 96, head 100, and deformed tail 98. Body 96 may be a solid body (e.g., as shown in FIG. 6) or a body that include an inner lumen (e.g., as shown in FIG. 8). Head 100 has a flanged portion that is located below conductive plate 60A. Similarly, deformed tail 98 has a flanged portion that is located above tab 78A, which is the "top" tab of the stack. In the example of FIGS. 5 and 6, spacer 86D is between tail 98 and tab 78A. In such an example, spacer 86D may be thicker and other more structurally rigid than tab 78A, e.g., to prevent head 98 of rivet 84 from "pulling-through" tab 78A if spacer 86D was not present. In other examples, tail 98 may be directly adjacent to tab 78A.

The flanged shape of head 100 and deformed tail 98 allows rivet 84 to fasten or otherwise mechanically attach cathode tabs 78, spacers 86, and conductive plate 60A to each other and prevent the stack from becoming detached from each other. As will be described in further detail below, before being deformed, tail 98 may be inserted into aperture 94 such that it extends out of the top of the stack of tabs 78, spacers 86, and conductive plate 60A. Subsequently, tail 98 is deformed to form the flange and attaches the stack of tabs 78, spacers 86, and conductive plate 60A together.

Rivet 84 may fix and define the thickness of the stack of tabs 78, spacers 86, and conductive plate 60A shown in the z-direction to correspond to the thickness of body 96 in the z-direction. In some examples, rivet 84 may apply a compressive force between head 100 and tail 98, e.g., to counteract a force in the other direction that would otherwise cause tabs 78 and spacers 86 from separating. In this manner, the stack of tabs 78 are prevented, e.g., from "fanning," e.g., spreading apart in the z-direction, during the operating life of battery 26 and preventing tabs 78 from losing electrical interconnect between each other.

In some examples, rivet 84 is configured to keep the stack of tabs 78 together such that weld(s) 92 does not receive the "book opening" mechanical loading. Weld(s) 92 may be present in assemblies including rivet 84 in stack of tabs 78 to provide a robust electrical connection, e.g., between the respective tabs. Long-term, corrosion and surface oxidation may degrade the interface contacts, thus, the need for the weld.

In some examples, the height (in the Z-direction) of rivet 84 is selected based on the stack modeling described above. The modeling work may suggest just one rivet for all production variation options, or if too variable, the individual tab/spacer stacks can be actively measured during manufacturing before selecting any of several premade rivet heights for a particular stack.

Rivet 84 may be formed from any suitable material such as stainless steel (e.g., 300 series stainless steel), monel or other nickel-copper alloy, and/or nickel. In some examples, rivet 84 may be an electrically conductive material such that rivet 84 functions to electrically couple the individual tabs 78, spacers 86, and conductive plate 60A together, e.g., alone or in combination with other features such as welds 92 and/or conductive spacers 86. In other examples, rivet 84 may be formed of an electrically insulating material.

Figure 7:
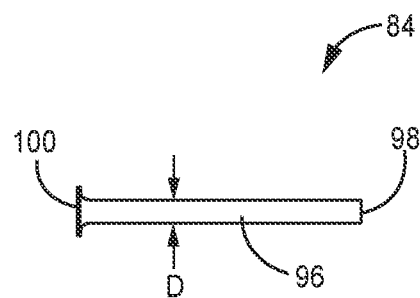
FIG. 7 is a conceptual diagram illustrating an example rivet that may be included in a battery assembly.

FIG. 7 is a photograph illustrating example rivet 84 that may be employed in examples of the disclosure. Rivet 84 include head 100, tail 98, and body 96 that extends between head 100 and tail 98. Rivet 84 is shown in a state prior to tail 98 being deformed as shown in FIG. 6, for example. Body 96 of rivet 84 has an outer diameter D that is smaller than the size of aperture 94 extending through the stack of tabs 78, spacers 86, and conductive plate 60A shown in FIGS. 5 and 6. In some examples, body 96 of rivet 85 may have an outer diameter of about 28 mils or less, e.g., with the diameter of head 100 and deformed tail 98 being about 40 mils or greater. In examples in which body 96 includes an inner lumen rather than being solid, the thickness of the body walls may be about 5 mils. In some examples, the overall length of rivet 84 from head 100 to tail 98 may be about 272 mils or less. In some examples, the overall height (in the Z-direction) of the combination of tabs 78 and spacers 86 may be about 0.230 inches (e.g., +/−0.03 inches). Other values are contemplated.

Figure 9:
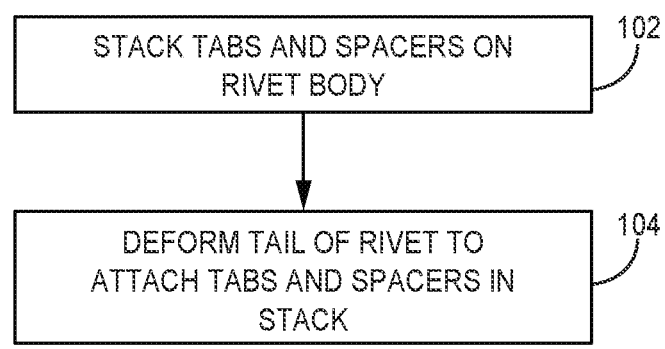
FIG. 9 is a flowchart illustrating an example technique in accordance with examples of the disclosure.

FIG. 8 is a schematic diagram illustrating an example apparatus 106 for deforming tail 98 when arranged with cathode tabs 78 and spacers 86 to form a stacked assembly in which tabs 78 and spacers 86 are attached to each other via rivet 84. FIG. 9 is a flowchart illustrating an example technique for attaching tabs 78 and spacers 86 to each other via rivet 84. For ease of description, the example technique of FIG. 9 will be described with regard to apparatus 106 shown in FIG. 8.

As shown in FIG. 9, tabs 78 and spacers 86 may be stacked on body 96 of rivet 84 (102). For example, aperture 94 of the individual tabs of tabs 78 and individual spacers 86 may be sequentially placed over tail 98 onto body 96 in the order and arrangement desired, e.g., in the arrangement shown in FIG. 8. In other examples, tabs 78 and spacers 86 may be arranged in a stack initially with apertures aligned (e.g., using a fixture pin) and then placed as a single stack onto body 96 over tail 98. The stacking may be accomplished manually or by robotic assembly devices (e.g., a pick and place robotic device).

Once tabs 78 and spacers 86 are assembled over rivet 84, tail 98 may be deformed to attach tabs 78 and spacers 86 in the stacked arrangement (104). For example, retractable supports 110 may be used force swage 108 into tail 98 against fixed pin 112, e.g., via a compressive force, to deform the edges of tail 98 outwardly and form a flanged end as shown in FIG. 8. In some example, weld(s) 92 may then be formed, e.g., via laser welding or other suitable process, in tabs 78 and spacers 86 after rivet 84 has been installed. Alternatively, weld(s) 92 may be formed prior to installation of rivet 84.

The example of FIG. 9 illustrates only one example technique for deforming tail 98 of rivet 84 within aperture 94 in the stack of tabs 78 and spacers 86 to attach tabs 78 and spacers 86 to each other. Other examples suitable technique may be employed as well as other types of rivets, such as, e.g., rivets with solid bodies.

Figure 10:
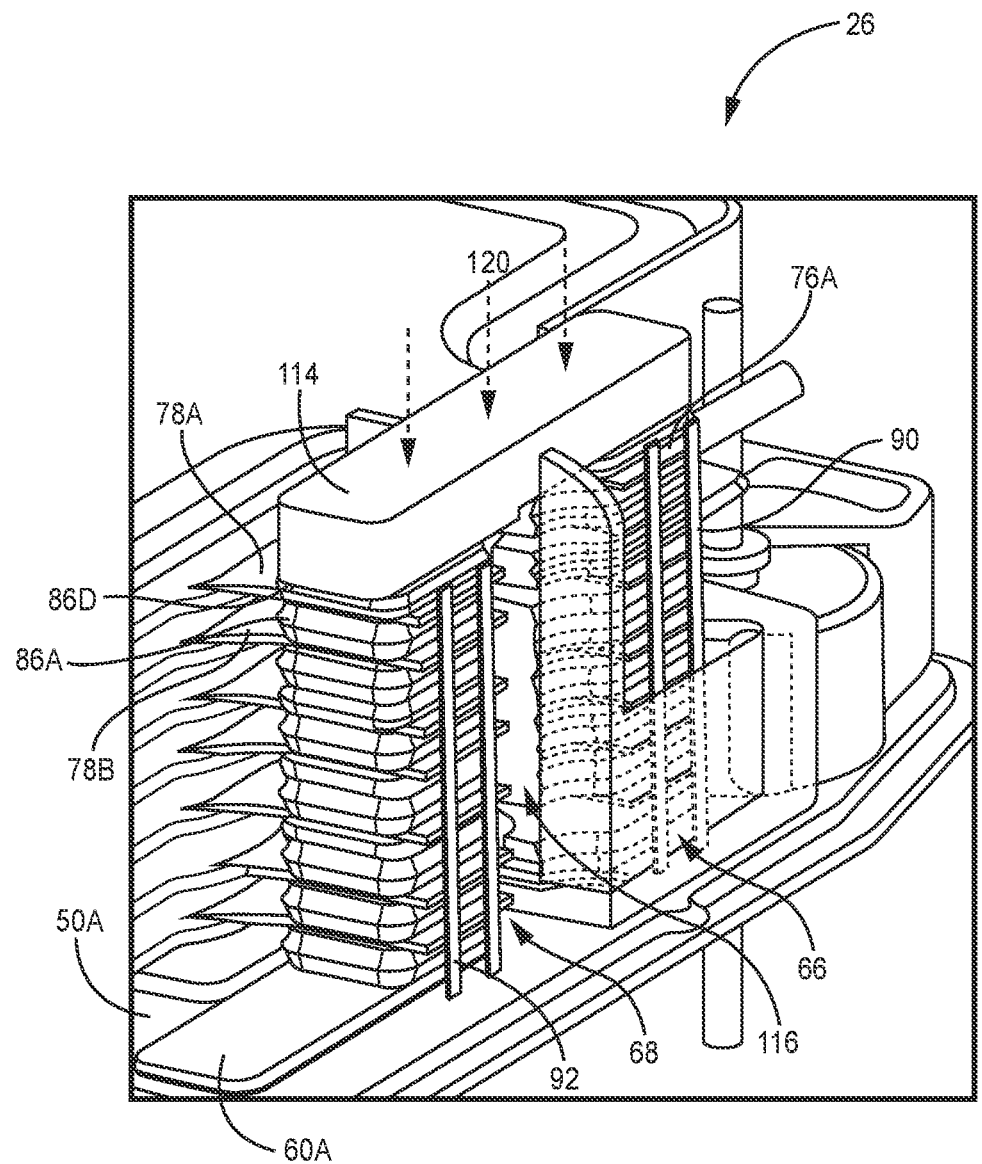
FIG. 10 is a conceptual diagram illustrating a portion of an example battery assembly in accordance with examples of the disclosure.

As noted above, some example battery assemblies of the disclosure may additionally, or alternatively, include a shim on the "top" of the stack of tabs 78 and spacers 86, e.g., to prevent "fanning" of the tabs 78 as described herein. FIG. 10 is a schematic diagram illustrating an example of battery 26 including shim 114. As shown in FIG. 10, shim 114 is located on stack of tabs 78 and spacers 86 of cathode stack 68. In the example of FIG. 10, shim 114 is not directly on top of tab 78A but instead is separated from tab 78A by spacer 86D. In other examples, shim 114 may be located directly on tab 78A. Although not shown in FIG. 10, in some examples, welds 92 may be extended to include shim 114 along the side of the stack assembly depending on the material used to form shim 114.

Additionally, shim 114 is located on stack of tabs 76 of anode stack 66 in a similar fashion. Shim 114 is a single member that spans gap 116 between stack of tabs 78 of cathode stack 68 and stack of tabs 76 of anode stack 66, which also includes spacers (not labelled) between the individual tabs in the stack. While shim 114 is a single member in the example of FIG. 10, in other examples, battery 26 may include one shim located on the stack of tabs and spacers for cathode stack 68 and another shim located on the stack of tabs and spacers for anode stack 66.

In some examples, rather than being a separate component, shim 114 may be included as an integral feature of another component, e.g., of an insulative component. For example, in some examples, shim 114 may be a portion of another typical insulator used to isolate electrical polarities within the battery 26, e.g., a headspace insulator, a stack insulator, and/or a feedthrough insulator. In some examples, shim 114 may be attached or otherwise included as a foldable feature of the component to allow for ease of assembling battery 26, while also preventing against the occurrence of inadvertently not being installed during the assembly of battery 26.

Although not shown in FIG. 10, when battery housing 50 is assembled with top portion 50B (shown in FIG. 2) and bottom portion 50A being sealed or otherwise attached to each other to form housing 50, the thickness of shim 114 (in the z-direction) may be selected such that the top surface of shim 114 comes into contact with the inner surface of top portion 50B of battery housing 50. In some examples, the contact between the top surface of shim 114 and the inner surface of top portion 50B of housing 50 may apply a compressive force (represented by arrows 120 in FIG. 10) or otherwise prevent cathode stack 68 and anode stack 66 from fanning. For example, when top portion 50B is attached to bottom portion 50A of housing 50, e.g., via a weld around the perimeter of housing 50 at the interface between top and bottom portion 50B and 50B, compressive force 120 may be applied to the stack of tabs 78 of cathode 68 and the stack of tab 76 of anode 66 between the top and bottom portions 50B and 50A by way of shim 114. In this manner, compressive force 120 may prevent the stack of tabs 78 of cathode 68 and the stack of tab 76 of anode 66 from "fanning," e.g., during the operating life of battery 26.

Shim 114 may be formed of any suitable material. In some examples, shim 114 may be formed of an electrically insulating material, e.g., to prevent electrical coupling of cathode stack 68 and anode stack 66 by way of shim 114 and/or electrical coupling of cathode stack 68 and/or anode stack 66 to housing 50. Example insulating materials may include polypropylene, polyethylene, and/or the like. In other example, shim 114 may be formed of an electrically conductive material, such as titanium, stainless steel, and/or the like. In some examples, spacer 86D between top tab 78A of cathode 68 as well as the spacer between shim 114 and top tab 76A of anode 66 may be electrically insulating to prevent electrical coupling between the respective electrode tabs and shim 114. In other examples, shim 114 may be configured such that the compressive force is applied once the cathode stack 68 and/or anode stack 66 begin to start fanning, e.g., at some point during the operating life of battery 26.

Figure 11:
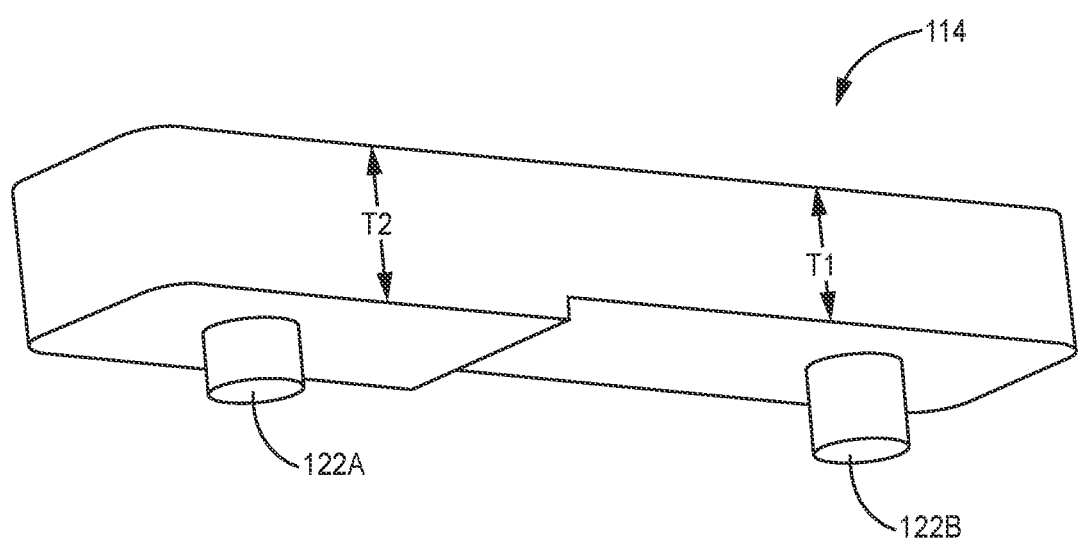
FIG. 11 is a conceptual diagram illustrating the example shim shown in FIG. 10.

FIG. 11 is a schematic diagram illustrating an example of shim 114. As shown, shim 114 does not have a constant thickness but instead exhibits a thickness T1 on one side of shim 114 and thickness T2 on the other side of shim 114. This difference in this may account for the differences in distance between the tab/spacer stack of cathode stack 68 and the inner surface of top portion 50B of housing 50 compared to the distance between the tab/spacer stack of anode stack 66 and the inner surface of top portion 50B of housing 50 when housing 50 is assembly around the internal components of battery 26.

As shown, in some examples, shim 114 may include posts 122A and 122B. Post 122A may be configured to fit within a portion of aperture 94 of the stack of tabs 78 and spacers 86 of cathode stack 68. Similarly, post 122B may be configured to fit within a portion of a similar aperture in the stack of tabs/spacers of anode stack 66. This feature may facilitate the registration or alignment of shim 114 with respect to anode stack 66 and cathode stack 68, and maintain shim 114 in place, e.g., before, during, and/or after top portion 50B and bottom portion 50A of housing 50 are assembled. Such a design may be utilized in cases in which a rivet, such as, rivet 84, does not extend through the stack of tabs and spacers of the anode stack and cathode stack. For examples including a rivet in one or both of the anode stack and cathode stack, shim 114 may include another type of registration feature (e.g., indentions into shim 114 rather than protrusion such as posts 122A and 122B) other than that shown in FIG. 11, e.g., so that the rivet and shim may both prevent fanning of the stack of tabs during the operating life of the battery.

Figure 12:
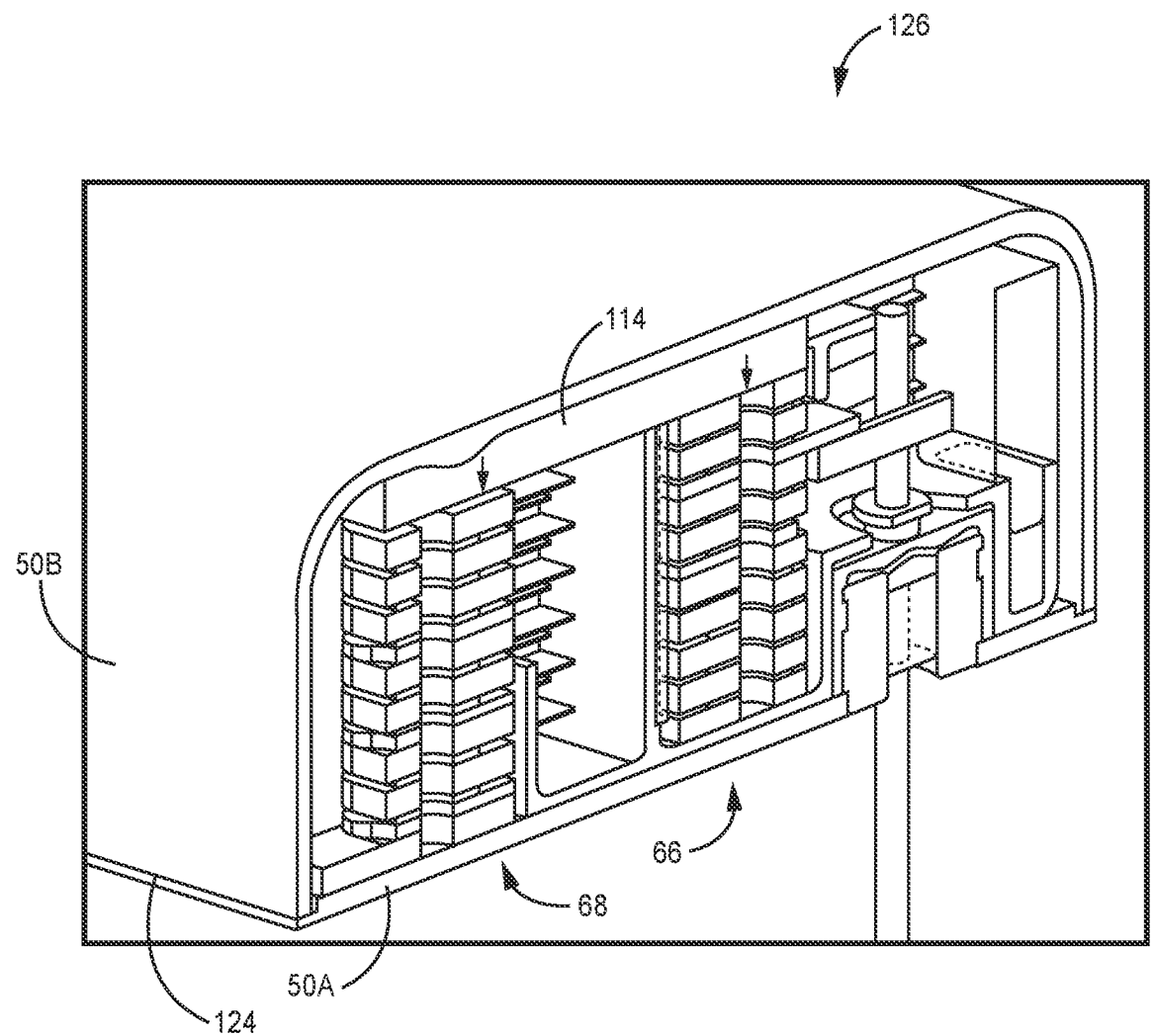
FIG. 12 is a conceptual diagram illustrating the example battery including an example shim.

FIG. 12 is a conceptual diagram illustrating another example battery 126. Battery 126 may be similar to the other battery assemblies described herein and like features are numbered similarly. FIG. 12 illustrates an example in which shim 114 is employed between the inner surface of the top portion 50B of housing 50 and cathode stack 68 and anode stack 66. As described above, the contact between the top surface of shim 114 and the inner surface of top portion 50B of housing 50 may apply a compressive force (represented by the two arrows in FIG. 12) or otherwise prevent cathode stack 68 and anode stack 66 from fanning. For example, when top portion 50B is attached to bottom portion 50A of housing 50, e.g., via a weld around the perimeter of housing 50 at the interface between top and bottom portion 50B and 50B, the compressive force may be applied to the stack of tabs 78 of cathode 68 and the stack of tab 76 of anode 66 between the top and bottom portions 50B and 50A by way of shim 114. In this manner, the compressive force may prevent the stack of tabs 78 of cathode 68 and the stack of tab 76 of anode 66 from "fanning," e.g., during the operating life of battery 126. In some examples, shim 114 may be configured such that the compressive force is applied once the cathode stack 68 and/or anode stack 66 begin to start fanning, e.g., at some point during the operating life of battery 126.

Various examples have been described in the disclosure. These and other examples are within the scope of the following clause and claims.

Clause 1. A battery assembly for an implantable medical device, the assembly comprising: an electrode stack comprising a plurality of electrode plates, wherein the plurality of electrode plates comprises a first electrode plate including a first tab extending from the first electrode plate and a second electrode plate including a second tab extending from the second electrode plate; a spacer between the first tab and the second tab; and
  a rivet extending through the first tab, second tab, and spacer, wherein the rivet is configured to mechanically attach the first tab, second tab, and spacer to each other.

Clause 2. The assembly of clause 1, wherein the rivet comprises a flared head, a deformed tail, and a rivet body extending between the flared head and deformed tail, and wherein the flared head is on a first side of the electrode stack, and the deformed tail on a second side of the electrode stack.

Clause 3. The assembly of clause 1, wherein the spacer comprises a first spacer, wherein the plurality of electrode plates includes a third electrode plate including a third tab extending from the third electrode plate, wherein the second tab is between the first tab and the third tab, the assembly further comprising a second spacer between the third tab and the second tab, wherein the rivet extends through the third tab and the second spacer.

Clause 4. The assembly of clause 3, wherein the first spacer has a first thickness different from a second thickness of the second spacer.

Clause 5. The assembly of clause 1, wherein the spacer comprises a first spacer, the assembly further comprising a second spacer between the first tab and second tab adjacent the first spacer.

Clause 6. The assembly of clause 1, further comprising a weld on the electrode stack extending from the first tab to the second tab across the spacer.

Clause 7. The assembly of clause 1, wherein the first electrode plate is the top plate in the plurality of electrode plates of the electrode stack, the assembly further comprising: a battery housing that encloses the electrode stack; and a shim located on top of the first tab between the first tab and an inner surface of the battery housing.

Clause 8. The assembly of clause 7, wherein the first electrode plate comprises a first anode plate and the second electrode plate comprises a second anode plate, wherein the plurality of electrode plates further comprises a first cathode plate including a third tab extending from the first cathode plate and a second cathode plate including a fourth tab extending from the second cathode plate, wherein the third tab and second tab are stacked adjacent to the first tab and second tab, and wherein the top spacer spans a gap between the first tab and the third tab.

Clause 9. The assembly of clause 7, wherein the top spacer is formed of an electrically insulative material to electrically isolate the first tab from the battery housing.

Clause 10. A battery assembly for an implantable medical device, the assembly comprising: a battery housing; an electrode stack comprising a plurality of electrode plates, wherein the plurality of electrode plates including a first tab stack of anode tabs extending from anode plates of the electrode stack and a second tab stack of cathode tabs extending from cathodes plates of the electrode stack, wherein the first tab stack is adjacent to the second tab stack and a gap separates the first tab stack from the second tab stack; and a shim located on a top tab of at least one of the first tab stack or the second tab stack, wherein the shim is located between the at least one of the first tab stack or the first tab of the second tab stack and the battery housing.

Clause 11. The battery assembly of clause 10, wherein the shim spans the gap between the first tab stack and the second tab stack.

Clause 12. The assembly of clause 10, wherein the shim is formed of an electrically insulative material to electrically isolate the first tab stack and the second tab stack from the battery housing.

Clause 13. The assembly of clause 10, wherein the battery housing is configured to apply a compressive force to the first tab stack and the second tab stack via the shim.

Clause 14. The assembly of clause 10, wherein the second tab stack includes a first cathode tab and a second cathode tab, the assembly further comprising a first spacer located between the first cathode tab and the second cathode tab.

Clause 15. The assembly of clause 14, further comprising a second spacer between the first cathode tab and the second cathode tab, and wherein the first spacer has a thickness less than a thickness of the second spacer.

Clause 16. The assembly of clause 14, wherein the second tab stack includes a third cathode tab, the assembly further comprising a second spacer between the second cathode tab and the third cathode tab.

Clause 17. The assembly of clause 16, wherein the first spacer has a thickness less than a thickness of the second spacer.

Clause 18. The assembly of clause 10, further comprising a rivet extending through the second tab stack to mechanically attach the individual tabs of the second tab stack to each other.

Clause 19. The assembly of clause 18, wherein the rivet comprises a flared head, a deformed tail, and a rivet body extending between the flared head and deformed tail, and wherein the flared head is on a first side of the second tab stack, and the deformed tail on a second side of the second tab stack.

Clause 20. The assembly of clause 10, further comprising a weld on the second tab stack extending from a top tab of the second tab stack to a bottom tab of the second tab stack.

Clause 21. The assembly of clause 10, wherein the weld extends to the shim. Clause 22. The assembly of clause 10, wherein the shim includes a first protrusion configured to mate with an aperture in the first tab stack and a second protrusion configured to mate with an aperture in the second tab stack.

Clause 23. The assembly of clause 10, wherein the shim is configured to transfer a compressive force from battery housing to the at least one of the first tab stack or the second tab stack.

Clause 24. An implantable medical device comprising: an outer housing; processing circuitry; and the battery assembly of clause 1 within the outer housing, wherein the processing circuitry is configured to control delivery electrical therapy from the implantable medical device to a patient using power supplied by the battery assembly.

Clause 25. An implantable medical device comprising: an outer housing;
processing circuitry; and the battery assembly of clause 10 within the outer housing, wherein the processing circuitry is configured to control delivery electrical therapy from the implantable medical device to a patient using power supplied by the battery assembly.

Clause 26. A method comprising assembling any one of clauses 1-25.

The invention claimed is:

1. A battery assembly comprising:
a battery housing;
an electrode stack comprising a plurality of electrode plates, wherein the plurality of electrode plates including a first tab stack of anode tabs extending from anode plates of the electrode stack and a second tab stack of cathode tabs extending from cathodes plates of the electrode stack, wherein the first tab stack is adjacent to the second tab stack and a gap separates the first tab stack from the second tab stack; and
a shim located on a top tab of at least one of the first tab stack or the second tab stack, wherein the shim is located between the at least one of the first tab stack or the first tab of the second tab stack and the battery housing.

2. The assembly of claim 1, wherein the shim spans the gap between the first tab stack and the second tab stack.

3. The assembly of claim 1, wherein the shim is formed of an electrically insulative material to electrically isolate the first tab stack and the second tab stack from the battery housing.

4. The assembly of claim 1, wherein the battery housing is configured to apply a compressive force to the first tab stack and the second tab stack via the shim.

5. The assembly of claim 1, wherein the second tab stack includes a first cathode tab and a second cathode tab, the assembly further comprising a first spacer located between the first cathode tab and the second cathode tab.

6. The assembly of claim 5, further comprising a second spacer between the first cathode tab and the second cathode tab, and wherein the first spacer has a thickness less than a thickness of the second spacer.

7. The assembly of claim 5, wherein the second tab stack includes a third cathode tab, the assembly further comprising a second spacer between the second cathode tab and the third cathode tab.

8. The assembly of claim 7, wherein the first spacer has a thickness less than a thickness of the second spacer.

9. The assembly of claim 1, further comprising a weld on the second tab stack extending from a top tab of the second tab stack to a bottom tab of the second tab stack.

10. An implantable medical device system comprising:
an outer housing;
processing circuitry; and
a battery assembly within the outer housing, the battery assembly comprising:
a battery housing,
an electrode stack comprising a plurality of electrode plates, wherein the plurality of electrode plates including a first tab stack of anode tabs extending from anode plates of the electrode stack and a second tab stack of cathode tabs extending from cathodes plates of the electrode stack, wherein the first tab stack is adjacent to the second tab stack and a gap separates the first tab stack from the second tab stack, and
a shim located on a top tab of at least one of the first tab stack or the second tab stack, wherein the shim is located between the at least one of the first tab stack or the first tab of the second tab stack and the battery housing,
wherein the processing circuitry is configured to control at least one of the delivery electrical stimulation from the implantable medical device to a patient or sensing of electrical signals of the patient by the implantable medical device using power supplied by the battery assembly.

11. The system of claim 10, wherein the shim spans the gap between the first tab stack and the second tab stack.

12. The system of claim 10, wherein the shim is formed of an electrically insulative material to electrically isolate the first tab stack and the second tab stack from the battery housing.

13. The system of claim 10, wherein the battery housing is configured to apply a compressive force to the first tab stack and the second tab stack via the shim.

14. The system of claim 10, wherein the second tab stack includes a first cathode tab and a second cathode tab, the assembly further comprising a first spacer located between the first cathode tab and the second cathode tab.

15. The system of claim 14, further comprising a second spacer between the first cathode tab and the second cathode tab, and wherein the first spacer has a thickness less than a thickness of the second spacer.

16. The system of claim 14, wherein the second tab stack includes a third cathode tab, the assembly further comprising a second spacer between the second cathode tab and the third cathode tab.

17. The system of claim 16, wherein the first spacer has a thickness less than a thickness of the second spacer.

18. The system of claim 10, further comprising a weld on the second tab stack extending from a top tab of the second tab stack to a bottom tab of the second tab stack.

19. The system of claim 10, further comprising an implantable medical lead including at least one electrode electrically coupled to the battery assembly, wherein the processing circuitry is configured to control the delivery electrical stimulation from the implantable medical device to a patient using power supplied by the battery assembly by at least controlling the delivery of the electrical stimulation to the patient via the at least one electrode on the implantable medical lead.

20. The system of claim 10, wherein the electrical stimulation delivered to the patient includes as least one of pacing pulses, a cardioversion shock, or a defibrillation shock.

* * * * *